(12) United States Patent
Leonardi

(10) Patent No.: US 9,271,677 B2
(45) Date of Patent: Mar. 1, 2016

(54) INTRAOCULAR PRESSURE MEASURING AND/OR MONITORING DEVICE

(75) Inventor: Matteo Leonardi, Pully (CH)

(73) Assignee: Sensimed SA, Lausanne (CH)

( * ) Notice: Subject to any disclaimer, the term of this patent is extended or adjusted under 35 U.S.C. 154(b) by 102 days.

(21) Appl. No.: 14/349,714

(22) PCT Filed: Oct. 5, 2011

(86) PCT No.: PCT/EP2011/067408
§ 371 (c)(1),
(2), (4) Date: Apr. 4, 2014

(87) PCT Pub. No.: WO2013/050073
PCT Pub. Date: Apr. 11, 2013

(65) Prior Publication Data
US 2014/0243645 A1 Aug. 28, 2014

(51) Int. Cl.
*A61B 3/16* (2006.01)
*A61B 5/00* (2006.01)

(52) U.S. Cl.
CPC ............. *A61B 5/6821* (2013.01); *A61B 3/16* (2013.01); *A61B 5/0002* (2013.01); *A61B 5/742* (2013.01)

(58) Field of Classification Search
CPC ....... A61B 3/16; A61B 5/0002; A61B 5/6821
USPC ......................................................... 600/398
See application file for complete search history.

(56) References Cited

U.S. PATENT DOCUMENTS 4,922,913 A    5/1990   Waters, Jr. et al.

FOREIGN PATENT DOCUMENTS

| GB | 2464981 A | 5/2010 |
|----|-----------|--------|
| WO | 2009/049686 A1 | 4/2009 |
| WO | 2011/083105 A1 | 7/2011 |

OTHER PUBLICATIONS

Matteo Leonardi et al., "First Steps toward Noninvasive Intraocular Pressure Monitoring with a Sensing Contact Lens", Investigative Ophthalmology & Visual Science, Sep. 30, 2004, pp. 3113-3117, vol. 45, No. 9.
Matteo Leonardi et al., "Wireless Contact Lens Sensor for Intraocular Pressure Monitoring: Assessment on Enucleated Pig Eyes", Acta Ophthamologica, Jun. 1, 2009, pp. 433-437, vol. 87, No. 4.
International Search Report and Written Opinion for PCT/EP2011/067408, dated Nov. 24, 2011.

*Primary Examiner* — Brian Szmal
(74) *Attorney, Agent, or Firm* — Bachman & LaPointe, P.C.

(57) ABSTRACT

Intraocular pressure measuring and/or monitoring device comprising a soft contact lens and a pressure sensor united with the soft contact lens, the pressure sensor being located such that it is applied against an eye of a user for sensing the intraocular pressure (IOP) of the eye when the soft contact lens is worn by the user, wherein the soft contact lens is softer than a surface of the eye and is configured to adapt its shape to the shape of the eye under the effect of capillary force maintaining the contact lens on the eye when the user is wearing the contact lens.

17 Claims, 3 Drawing Sheets

INTRAOCULAR PRESSURE MEASURING AND/OR MONITORING DEVICE

BACKGROUND OF THE INVENTION

The present invention relates to a device for measuring and/or monitoring the intraocular pressure (IOP). The present invention relates in particular to a device that can be placed on the eye of a user to monitor intraocular pressure over an extended period of time, for example 8 hours, 12 hours, 24 hours or more.

Glaucoma is a widespread disease characterized by an elevated intraocular pressure (IOP). This elevated IOP produces a gradual loss of peripheral vision. There is therefore a need to have a detailed knowledge of IOP in glaucoma patients in order to provide reliable diagnostics or for setting up new therapies.

U.S. Pat. No. 4,922,913 describes an intraocular pressure sensor having a piezo-resistance strain gauge cell mounted in a curved holder which serves to position the planar pressure sensitive surface of the strain gauge cell against the surface of an eye. This sensor is specifically designed to be placed on the sclerotic portion of the eyeball (sclera), so that the pressure sensitive surface presses on the white part of the eye. The sensor is small, so that, when placed on the sclera, it is off-centered relative to the eye and it doesn't cover the cornea. The curved holder is made similarly to a hard contact lens.

A drawback of this intraocular pressure sensor is that it cannot be worn without interruption over extended periods of time because, like hard contact lenses, such a rigid holder rapidly provokes unbearable discomfort. Furthermore, the sensor is connected with wires to an external recording/monitoring apparatus, which is uncomfortable and requires that the recording/monitoring apparatus is kept relatively close to the user's head.

Another drawback of the pressure sensor of U.S. Pat. No. 4,922,913 is that a hard and small off-centered curved holder will significantly slide and move on the eyeball, thus resulting in uncontrolled changes of the measurements' conditions and thereby compromising the accuracy of the IOP measurement. In order to avoid significant displacements and to maintain it in good contact with the eyeball, the curved holder of U.S. Pat. No. 4,922,913 must be placed under the eyelid.

Yet another drawback of this intraocular pressure sensor is that the rigid holder must be manufactured or at least customized specifically for each user. A hard holder must indeed be perfectly adapted to the particular shape and size of the user's eyeball for it to properly fit and not disturb the user when worn. This individualization of the sensor thus increases its manufacturing costs.

SUMMARY OF THE INVENTION

An aim of the present invention is therefore to provide an intraocular pressure monitoring device that can adapt to a large number of users without specific customization.

Another aim of the present invention is to provide an intraocular pressure monitoring device that is comfortable for the user to wear without interruption on extended periods of time.

Yet another aim of the present invention is to provide a reliable intraocular pressure monitoring device.

These aims and other advantages are achieved by a device, a kit and a system comprising the features of the corresponding independent claim.

These aims are achieved in particular by an intraocular pressure measuring and/or monitoring device comprising a soft contact lens and a pressure sensor united with, for example embedded in, the soft contact lens, the pressure sensor being located such that it is applied against an eye of a user for sensing the intraocular pressure (IOP) of the eye when the soft contact lens is worn by the user, wherein the soft contact lens is softer than a surface of the eye and is configured to adapt its shape to the shape of the eye under the effect of a suction force generated by capillary force of the tear film under the contact lens and maintaining it on the eye when the user is wearing the contact lens.

Since the device of the invention, in particular the contact lens, adapts to the cornea instead of the cornea adapting to the contact lens, it ensures minimal invasiveness of the device and highest measurement quality and accuracy.

The capillary force that generates the suction force is given by the tension force at the liquid-air interface and by the pressure drop in the tear film. The major component on the capillary force is due to the pressure drop in the tear film and so the suction force can be approximated by:

$$F_{suction} \cong A_{tear\,film} * \Delta P_{tear\,film} \cong A_{tear\,film} * 2 * \gamma * \cos(\Theta)/t,$$

where $A_{tear\,film}$ is the area wetted by the tear film under the contact lens, $\gamma$ is the surface tension of the tear film, $\Theta$ is the contact angle between tear film and contact lens and t is the thickness of the tear film.

In order to obtain a suitable and constant suction force, the contact lens surface can be treated or coated to decrease the contact angle and therefore to increase the capillary force. For instance, pure silicone has a typical contact angle between 100° and 110°, which can be reduced to less than 50° with an oxygen plasma treatment.

These aims are achieved also by a kit comprising such an intraocular pressure measuring and/or monitoring device and a portable recording device configured for communicating with the intraocular pressure measuring and/or monitoring device and for storing data received from the intraocular pressure measuring and/or monitoring device.

These aims are furthermore achieved by an intraocular pressure monitoring system comprising such an intraocular pressure measuring and/or monitoring device, a portable recording device configured for communicating with the pressure measuring and/or monitoring device and for storing data received from the intraocular pressure measuring and/or monitoring device, and a computing device configured for communicating with the portable recording device for receiving and/or processing and/or storing data received from the portable recording device.

In embodiments, the contact lens of the intraocular pressure measuring and/or monitoring device is made of a transparent hydrogel containing water in a concentration greater than 10% or of silicone hydrogel.

In other embodiments, the contact lens of the intraocular pressure measuring and/or monitoring device is made of a transparent pure silicone with water concentration less than 0.5%. An advantage of pure silicone is that it can be a good insulating material for the embedded sensor and electronics and that it remains stable in different moisture conditions because it doesn't swell.

In embodiments, the pressure sensor of the intraocular pressure measuring and/or monitoring device comprises a pressure sensitive membrane that is applied against the eye for sensing the intraocular pressure (IOP) of the eye when the soft contact lens is worn by the user. The pressure sensor is for example a piezoresistive pressure sensor and the membrane comprises piezo-resistors, for example four piezo-resistors in a Wheatstone bridge configuration.

The pressure sensor can be an absolute pressure sensor or a relative pressure sensor.

In embodiments, the pressure sensor is located in a cavity formed in an inner concave side of said contact lens. The cavity is filled with a gel or any other adapted soft and pressure transparent filler material, i.e. a filler material that doesn't interfere with pressure measurement. The gel or other filler material covers the pressure sensor such that a layer of the gel or filler material is located between the pressure sensor and the surface of the eye when the user is wearing the contact lens. The filler material is for example a silicone gel. The filler material is for example softer than or as soft as the material of the contact lens. In a particular embodiment, the filler material is the same material as the material of the contact lens. The cavity is for example a circular groove around the centre of the contact lens, or is formed in the centre of the contact lens. The external surface of the gel is for example convex, concave, flat, square, or of any other structured or unstructured shape for ensuring a constant and tight contact to the surface of the eye.

Hard and soft contact lenses are described in ISO norm 18369, which is incorporated herein by reference.

Rigid or hard contact lenses are made of transparent optical-grade plastics, such as polymethylmethacrylate (PMMA), cellulose acetate butyrate (CAB), polyacrylate/siloxane copolymers, rigid polysiloxanes (silicone resins), butylstyrenes, fluoropolymers, fluorosiloxanes, etc. that are harder than the surface of the eye of a user. Soft contact lenses however are made of materials that are easily deformable and softer than the surface of a human eye. A very large subset of soft contact lenses consists of transparent hydrogels containing water in concentrations greater than 10%. Soft contact lenses can also be made of non-hydrogel materials, e.g. flexible polysiloxanes (silicone elastomers).

Semi-rigid or semi-hard contact lenses commonly refer to rigid contact lenses made of a gas-permeable material.

Hard and/or semi-rigid contact lenses thus maintain their shape when placed on the cornea and/or on the sclera of a human eye. Therefore, if the shape of the hard contact lens is not perfectly adapted to the shape of the eyeball, it will locally deform and/or hurt the wearer's eye. Furthermore, the lens will easily slide over the eyeball's surface and/or pop out of the eye.

Soft contact lenses, however, are less rigid, or softer, than the cornea of a human eye. Therefore, when placed on the eyeball, the shape of the soft contact lens will adapt to the shape of the user's cornea, thereby minimizing disturbances for the user and maximizing the adherence of the lens to the eyeball under the effect of a suction force generated by capillary force of the tear film under the contact lens.

The soft contact lens of the intraocular pressure measuring and/or monitoring device of the invention thus allows obtaining a constant force, sufficient for maintaining the intraocular pressure measuring and/or monitoring device in a stable position on the eyeball, thereby allowing reliable IOP measurements. Since the pressure sensor remains in good mechanical contact with a same measuring point on the eye's surface, the IOP measurement performed by the IOP monitoring device of the invention is furthermore consistent, thus allowing an accurate monitoring of the IOP over time. The soft contact lens would be preferably larger than the corneo-scleral junction with a typical diameter of 14.1 mm and typical radius of curvature between 8.4 and 9 mm, but it can also be designed much larger and going well over the sclera, thereby further improving the stability on the eye of the IOP measuring and/or monitoring device of the invention. In order to ensure the ability of the contact lens to adapt to the eye shape, as discussed above, the contact lens has to be softer than the cornea and sclera and this is achieved by the combination of a soft material and its thickness. For instance, if the contact lens of the intraocular pressure measuring and/or monitoring device is made of a transparent pure silicone with a typical modulus of elasticity between 2-8 MPa, this can be achieved by a contact lens thickness of less than 1 mm in the centre and less than 0.5 mm in the periphery.

Another advantage of the intraocular pressure measuring and/or monitoring device of the invention is that the adhesion force of the soft contact lens onto the eye is constant over the surface of the contact lens which adapts to the shape of eye, such that the pressure sensor can be positioned anywhere within this area and relative to the center of the lens and still deliver a correct and reliable IOP measurement. This allows in particular positioning the pressure sensor off-centered on the soft contact lens in order to minimize or to completely avoid any sight impairment for the user wearing the soft contact lens.

Furthermore, the intraocular pressure measuring and/or monitoring device of the invention doesn't need to be customized for each user, because the soft contact lens easily adapts to different eye shapes and sizes. The soft contact lens can also be worn over a long period of time without discomfort for the user.

BRIEF DESCRIPTION OF THE DRAWINGS

The present invention will be better understood with the help of the following description illustrated by the figures, where.

DETAILED DESCRIPTION

Figure 1:
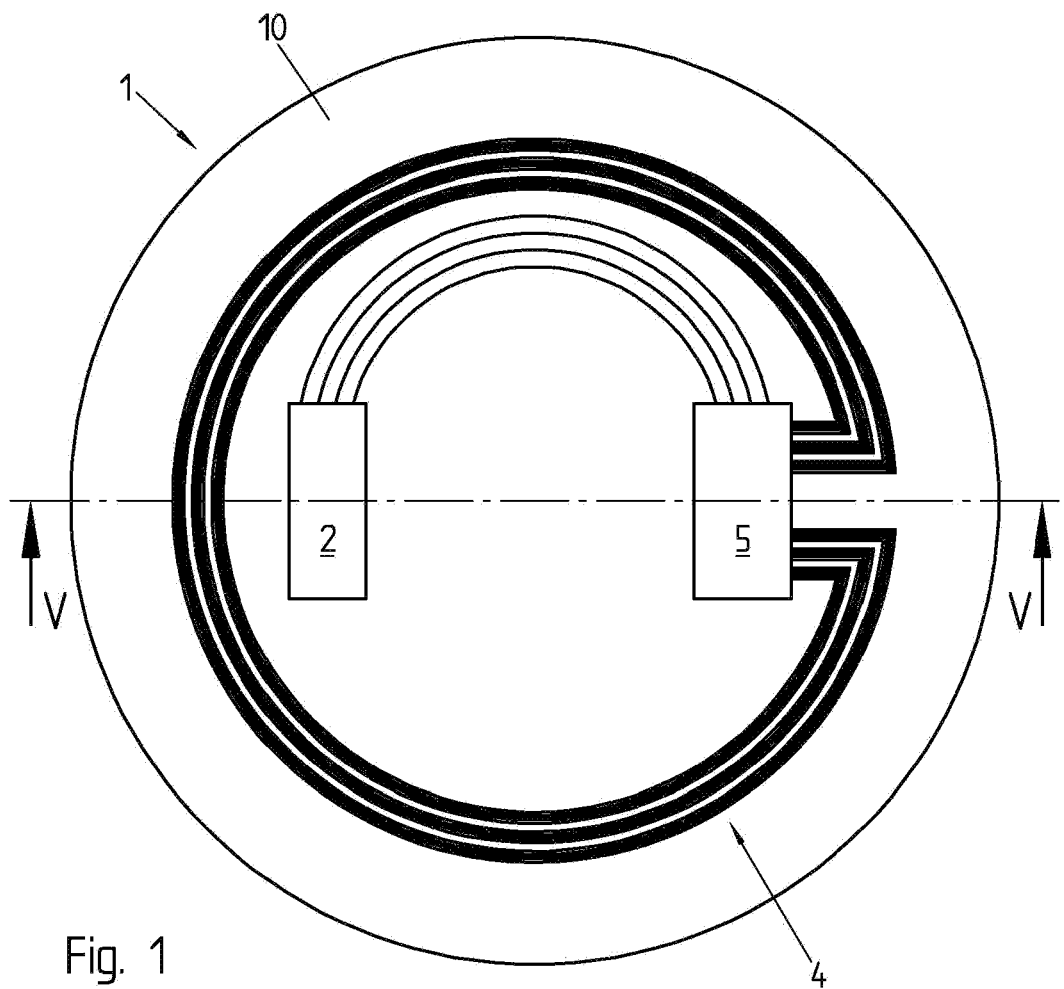
FIG. 1 shows an intraocular pressure measuring and/or monitoring device according to an embodiment of the invention.

In an embodiment illustrated in FIG. 1, the intraocular pressure measuring and/or monitoring device 1 comprises a pressure sensor 2 united with a contact lens 10, for example a soft contact lens. The pressure sensor 2 is located such that, when the contact lens 10 is worn by a user, the pressure sensor 2 is applied against an eyeball of the user for sensing the intraocular pressure (IOP) of the corresponding eye.

In the illustrated embodiment, the intraocular pressure measuring and/or monitoring device 1 further comprises, united with the contact lens 10, a microcontroller 5 in electrical contact with the pressure sensor 2 for powering the pressure sensor 2 and/or for receiving electrical signals from the pressure sensor 2 that correspond to the measured pressure, and an antenna 4 in electrical contact with the microcontroller 5 for wirelessly transmitting data, for example data related to the pressure measurement, to a remote equipment, for example to a remote recording and/or monitoring device, which is not represented in FIG. 1.

In an embodiment, the intraocular pressure measuring and/or monitoring device 1, in particular the microcontroller 5 and/or the pressure sensor 2, is preferably wirelessly inductively powered through the antenna 4, for example by the remote recording and/or monitoring device. In a variant embodiment, the pressure measuring and/or monitoring device comprises a power source, for example a battery or micro fuel cell or a wireless energy source like infrared or solar cells, for powering the microcontroller and/or the pressure sensor. The power source is for example located on or inside the contact lens, or on an external support, in which case it is for example electrically connected through thin and insulated electrical wires to the microcontroller and/or to the pressure sensor.

The pressure sensor 2 is for example a miniaturized pressure sensor comprising a piezoresistive silicon micromachined pressure sensor on a ceramic or silicon carrier. The pressure sensor 2 is either an absolute pressure sensor or a relative pressure sensor.

Figure 3:
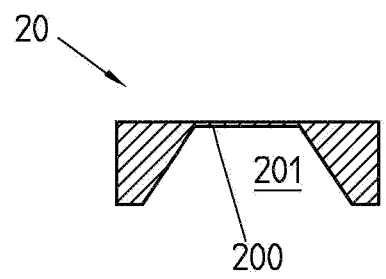
FIG. 3 is a cut view of a relative micromachined pressure sensor.
Figure 2:
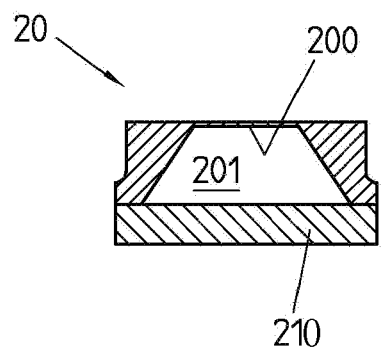
FIG. 2 is a cut view of an absolute micromachined pressure sensor.

FIG. 2 schematically illustrates an example of a piezoresistive silicon micromachined pressure sensor 20 for a relative pressure sensor, while FIG. 3 schematically illustrates a corresponding example of a piezoresistive silicon micromachined sensor 20 for an absolute pressure sensor.

According to the embodiments illustrated in FIG. 2 and in FIG. 3, the piezoresistive silicon micromachined sensor 20 comprises a sensitive silicon membrane 200 that stretches when a pressure applied on one of its sides is larger than the pressure applied on its other and opposite side. Piezo-resistors that are not represented in the figures, for example four piezo-resistors in a Wheatstone bridge configuration, are implanted in the silicon membrane 200 and sense the deformation of the membrane 200 by using the piezoresistive effect. The difference in pressure between the two opposite sides of the membrane 200 is thus determined by measuring the resistance of the circuit formed by the piezo-resistors, which depends on this pressure difference.

With reference to FIG. 1, measuring the pressure sensed by the pressure sensor 2 is for example performed in that the microcontroller 5 powers the pressure sensor 2 with a given voltage and receives in return from the pressure sensor 2 an electrical signal that corresponds to the sensed pressure, for example an electrical signal whose magnitude depends from the electrical resistance of the circuit formed by the piezo-resistors. The received signal is stored and/or processed for example in the microcontroller 5 for determining the measured pressure. The pressure measurement is for example performed at regular intervals, for example each time the intraocular pressure measuring and/or monitoring device 1 is inductively powered by an external device, for example an external RFID reader or similar. In variant embodiments, the pressure measurement is performed for example continuously or at randomly spaced intervals.

In a piezoresistive silicon micromachined sensor 20 for an absolute pressure sensor as illustrated by way of example in FIG. 2, a cavity 201 on the back side of the membrane 200 is sealed with a cap 210, for example a layer of pressure resistant glass. The cap 210 is for example affixed to the silicon micromachined sensor 20 by anodic bonding. The pressure inside the cavity 201 is a known reference pressure set before the bonding of the cap 210, for example vacuum. The pressure measured for example by the piezo-resistors of the membrane 200 is thus the difference between the pressure applied on the front side of the membrane 200 and the reference pressure inside the cavity 201. Since the reference pressure is constant, the absolute value of the pressure applied on the front side of the membrane is measured directly.

In a piezoresistive silicon micromachined sensor 20 for a relative pressure sensor as illustrated by way of example in FIG. 3, the cavity 201 at the back side of the membrane 200 is open, so that the pressure exerted on the back side of the diaphragm usually corresponds to the ambient pressure, for example to the atmospheric pressure. In embodiments, the open cavity 201 is for example filled with a soft pressure transparent material, for example with silicon gel, that doesn't interfere with pressure measurements. The pressure measured by the piezo-resistors of the membrane 200 is therefore the difference between the pressure applied on the front side of the membrane 200 and the ambient pressure.

An advantage of using a relative pressure sensor in the pressure monitoring device of the invention is that, if the pressure around the back side of the diaphragm corresponds to the ambient or atmospheric pressure, the pressure measured by the pressure sensor essentially corresponds to the intraocular pressure (IOP), free from the effects of the ambient or atmospheric pressure that are due for example to changes in altitude and/or weather conditions.

An advantage of using an absolute pressure sensor, on the other hand, is that it is much easier to embed in the contact lens for manufacturing.

The intraocular pressure measuring and/or monitoring device of the invention described in the above examples comprises a piezo-resistance pressure sensor. The use of other types of preferably MEMS-based relative or absolute pressure sensors, for example capacitive, resistive or piezo-electric pressure sensors, is however possible within the frame of the invention.

With reference to FIG. 1, the soft contact lens 10 is for example made of a transparent hydrogel containing water in a concentration greater than 10%, or of any other appropriate material having similar mechanical and/or optical properties, for example a flexible polysiloxane, a silicone elastomer, a pure soft silicone containing water in a concentration less than 0.5% or silicone-hydrogel. The soft contact lens 10 has a typical diameter of 14.1 mm and a typical radius of curvature between 8.4 and 9 mm and is softer than the surface of the eyeball of a user. Therefore, when the pressure measuring and/or monitoring device 1 is worn by a user, the soft contact lens 10 is slightly deformed, for example stretched, to adapt its shape to the shape of the eyeball, in particular to the curvature of the user's eye. This deformation of the contact lens 10 provides for a regular contact and a strong adherence between the contact lens 10 and the user's eyeball across the surface of the contact lens which adapts to the shape of the eye, thus providing for a close and constant contact between the pressure sensor 2 placed within this area and the eyeball.

Figure 4:
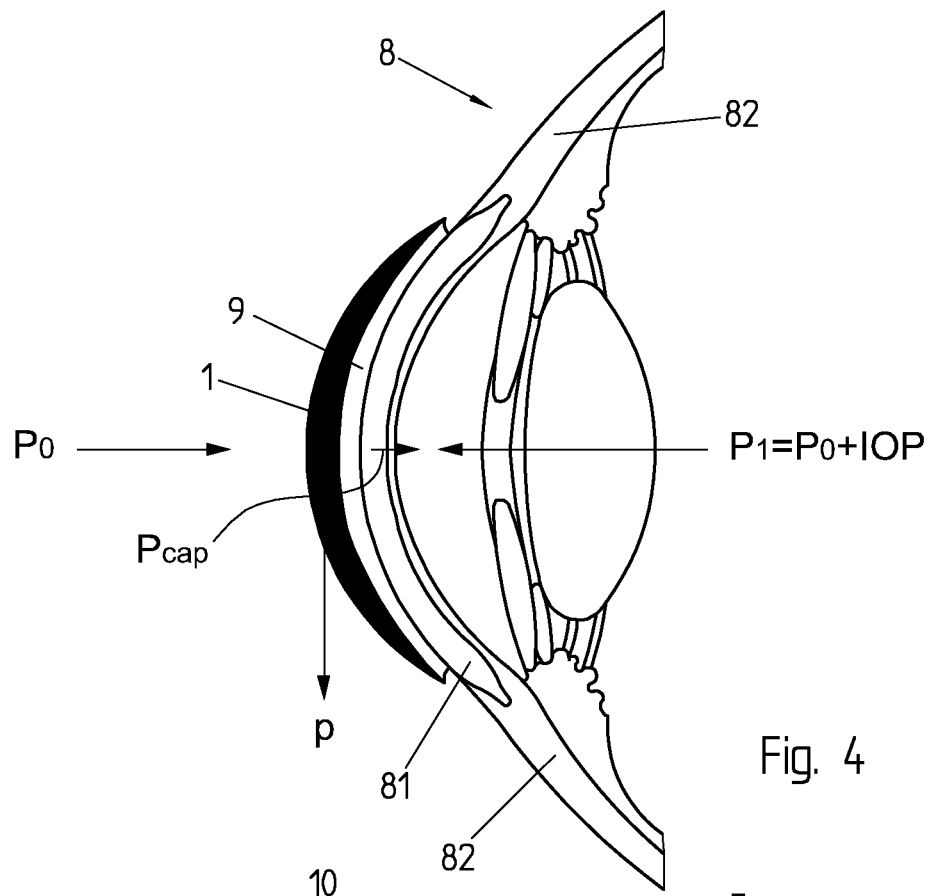
FIG. 4 illustrates the major pressures and forces acting on a soft contact lens placed on the eye of a user.

FIG. 4 is a cut view representing an intraocular pressure measuring and/or monitoring device 1 placed on the eye 8 of a user, for example on the cornea 81, with an illustration of the major pressures and forces present in this configuration.

These pressures and forces are:
 the external pressure around the eye $P_{ext}$, which corresponds to the atmospheric pressure $P_{atm}$;
 the internal hydrostatic pressure $P_{int}=P_{atm}+IOP$; where IOP is the intraocular pressure;
 the force of gravity p that is related to the weight of the pressure measuring and/or monitoring device 1;

the suction force $F_{suction}$, which is generated by the capillary force of the tear film 9 and retains the contact lens, i.e. the pressure measuring and/or monitoring device 1, on the eye 8.

The capillary force that generates the suction force is given by the tension force at the liquid-air interface 91 and by the pressure drop in the tear film 9. In order to obtain a suitable and constant suction force, the contact lens surface can be treated or coated to decrease the contact angle and therefore to increase the capillary force.

The interplay of the forces illustrated in FIG. 4 determines the fit of the pressure measuring and/or monitoring device 1. In normal conditions, i.e. in proper fitting conditions, there is a tear film 9 of about 2-12 μm in thickness between the soft contact lens of the pressure measuring and/or monitoring device 1 and the cornea 81, which lets the pressure measuring and/or monitoring device 1 slide on the cornea surface and find a stable balanced position. In this position, the soft contact lens of the pressure measuring and/or monitoring device 1 is slightly deformed and follows cornea deformations. This provides for a proper contact between the pressure sensor of the pressure measuring and/or monitoring device 1 and the surface of the eye 8.

Inside the eyeball, the hydrostatic pressure $P_{int}$ is the addition of the intraocular pressure IOP and of the atmospheric pressure $P_{atm}$, i.e. $P_{int}=P_{atm}+IOP$.

If the pressure sensor of the pressure measuring and/or monitoring device 1 is a relative pressure sensor with the ambient or atmospheric pressure $P_{atm}$ applied on the back side of its pressure sensing membrane and the hydrostatic pressure $P_{int}$ applied on the front side of said membrane, the measured pressure is thus equal to the intraocular pressure IOP of interest, corrected by a constant value k proportional to the suction force $F_{suction}$ that maintains the lens against the eye, thereby avoiding a step of correction and/or of calibration of the measured pressure for obtaining the IOP:

$$P_{measured}=P_{int}-P_{atm}+k=IOP+k$$

If the pressure sensor of the pressure measuring and/or monitoring device 1 is an absolute pressure sensor with for example vacuum or another reference pressure applied on the back side of its pressure sensing membrane and the hydrostatic pressure $P_{int}$ applied on the front side of said membrane, the measured pressure must furthermore be corrected by the variable ambient or atmospheric pressure $P_{atm}$ in order to determine the intraocular pressure IOP of interest:

$$P_{measured}=P_{int}+k=IOP+P_{atm}+k$$

The use of an absolute pressure sensor thus implies simultaneously measuring the local ambient or atmospheric pressure $P_{atm}$, for example with the help of another pressure sensor, for example external to the pressure measuring and/or monitoring device 1, for example in an external reading and/or recording apparatus.

FIG. 5 is a cut view of a pressure measuring and/or monitoring device 1 according to an embodiment of the invention. According to this embodiment, the pressure sensor 2 is placed in a cavity, for example an annular groove or a cavity of any other appropriate shape, formed on the inner and concave side of the contact lens 10. The pressure sensor 2 is placed in the cavity, which is then filled with a pressure transparent filler material 100 that doesn't interfere with pressure measurements, for example with gel or with silicone gel.

When the pressure measuring and/or monitoring device 1 is in a rest position, i.e. not worn by a user, the filler material 100 preferably slightly protrudes out of the cavity in which the pressure sensor 2 is placed, thus resulting in a for example convex external surface of the filler material 100 that forms a discontinuity in the inner and concave surface of the contact lens 10.

In embodiments, the filler material 100 is for example softer than the material of the soft contact lens 10, such that when the pressure measuring and/or monitoring device 1 is worn by a user and the contact lens 10 is applied against the surface of the user's eye, the external surface of the filler material 100 is pressed against the user's eye and deformed. The external surface of the filler material 100 thus perfectly adapts to the local shape of the eye's surface under the effect of the capillary force maintaining the contact lens 10 against the eye.

In variant embodiments, the filler material 100 and the contact lens 10 are made of the same material, for example silicone gel, and/or of materials having the same softness. In this case, the entire inner concave surface of the pressure measuring and/or monitoring device 1 equally adapts to the shape of the eye's surface.

When the pressure measuring and/or monitoring device 1 is worn, the filler material 100 forms a homogenous film between the pressure sensor 2, for example its sensitive membrane, and the surface of the eye. Since the filler material 100, for example a silicone gel, is pressure transparent, for example in that it is incompressible and yet deformable, the pressure at the eye's surface, i.e. the hydrostatic pressure, is integrally transmitted to the pressure sensor 2, for example to the front side of its pressure sensitive membrane. The pressure sensor 2 being covered on its front side with a thin layer of the filler material 100, for example a soft and flexible biocompatible silicone gel, the pressure sensor 2 is preferably not in direct contact with the eye, thereby avoiding allergic reactions or other discomforts to the user.

In variant embodiments, the external surface of the filler material is shaped and/or structured in order to improve the contact between the surface of the eye and the pressure sensor 2, and/or in order to achieve particular effects on the pressure measurement. The external surface of the gel 100 is structured for example as flat, concave, waved, square and protruding from the inner surface of the contact lens. Preferably, however, the surface of the gel 100 is shaped so that when the pressure measuring and/or monitoring device is placed onto the eye of a user it comes into contact with the eye's surface before the surrounding inner surface of the contact lens.

When the pressure measuring and/or monitoring device 1 of the invention is worn by a user, the soft contact lens 10 adheres with a constant force onto the user's eye within the adaptation area illustrated in FIG. 4, such that the pressure sensor 2 can be positioned anywhere in the soft contact lens 10 within this area and still be in good and constant contact with the eye's surface. As explained previously, the soft contact lens 10 adheres to the eye under a suction effect that is due to capillary force and is evenly distributed over the surface of the soft contact lens 10, which adapts to the shape of the eye thanks to the flexible nature of the lens's material. The pressure sensor is thus applied against the surface of the eye with an essentially constant force, thereby ensuring stable measurement conditions and thus reliable and coherent IOP measurements. Furthermore, the position of the worn pressure measuring and/or monitoring device 1 being essentially stable relative to the eye, the user's IOP is always measured essentially at the same location. This allows reproducible measurements over time, and thus a reliable monitoring of the IOP.

Figure 5A:
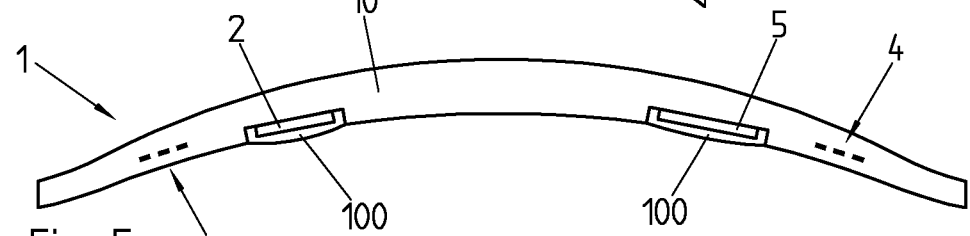
FIG. 5a is a cut view of the intraocular pressure measuring and/or monitoring device of FIG. 1 along the V-V line.
Figure 5B:
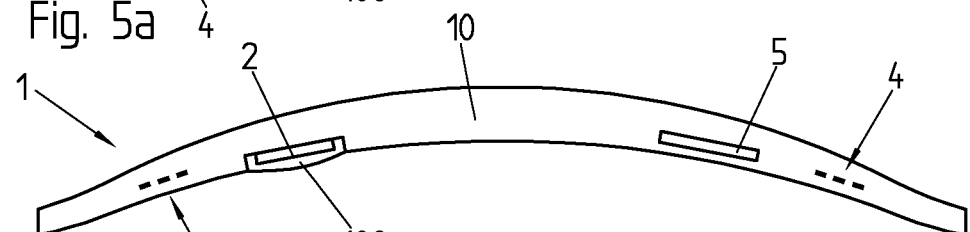
FIG. 5b is a cut view of a variant embodiment of the intraocular pressure measuring and/or monitoring device of the invention.

In the embodiments illustrated in FIGS. 5a and 5b, the pressure sensor 2 is located slightly out of the center of the contact lens 10 in order to minimize vision impairment for the user wearing the pressure measuring and/or monitoring device 1.

FIG. 5a illustrates an embodiment wherein the cavity formed in the contact lens 10 for lodging the pressure sensor 2 is a circular groove centered around the center of the contact lens 10. In this embodiment, the microprocessor 5 is for example also placed in the same cavity and covered with the filler material 100.

In the variant embodiment illustrated in FIG. 5b, the cavity is asymmetrical relative to the center of the contact lens 10, for example a round and off-centered cavity, a semi-annular groove or any other adapted shape. In this case, the microprocessor 5 is for example placed directly inside the contact lens 10.

Figure 6:
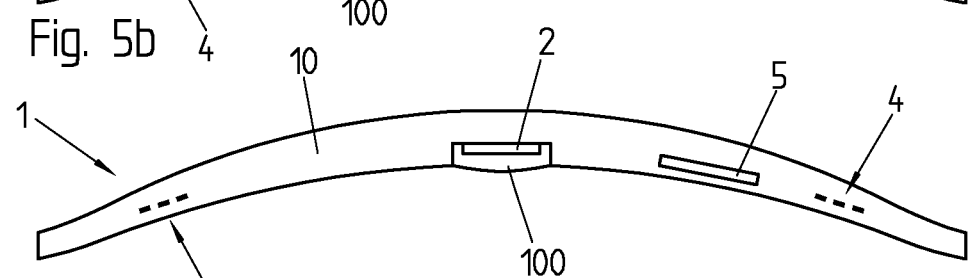
FIG. 6 is a cut view of an intraocular pressure measuring and/or monitoring device according to another embodiment of the invention.

In another embodiment illustrated in FIG. 6, the pressure sensor 2 is located in the center of the contact lens 10. According to this embodiment, the pressure sensor 2 is for example placed in a, for example circular, cavity formed in the center of the contact lens 10.

Other cavity shapes and/or locations are however possible within the frame of the invention for placing the pressure sensor 2 and/or other elements of the pressure measuring and/or monitoring device 1 in or on the contact lens 10.

Optionally, the pressure measuring and/or monitoring device 1 further comprises additional and/or other measuring devices such as for example an ElectroRetinoGraph, a chemical analysis sensor and/or a second pressure sensor of the same or of another type as the first one.

Figure 7:
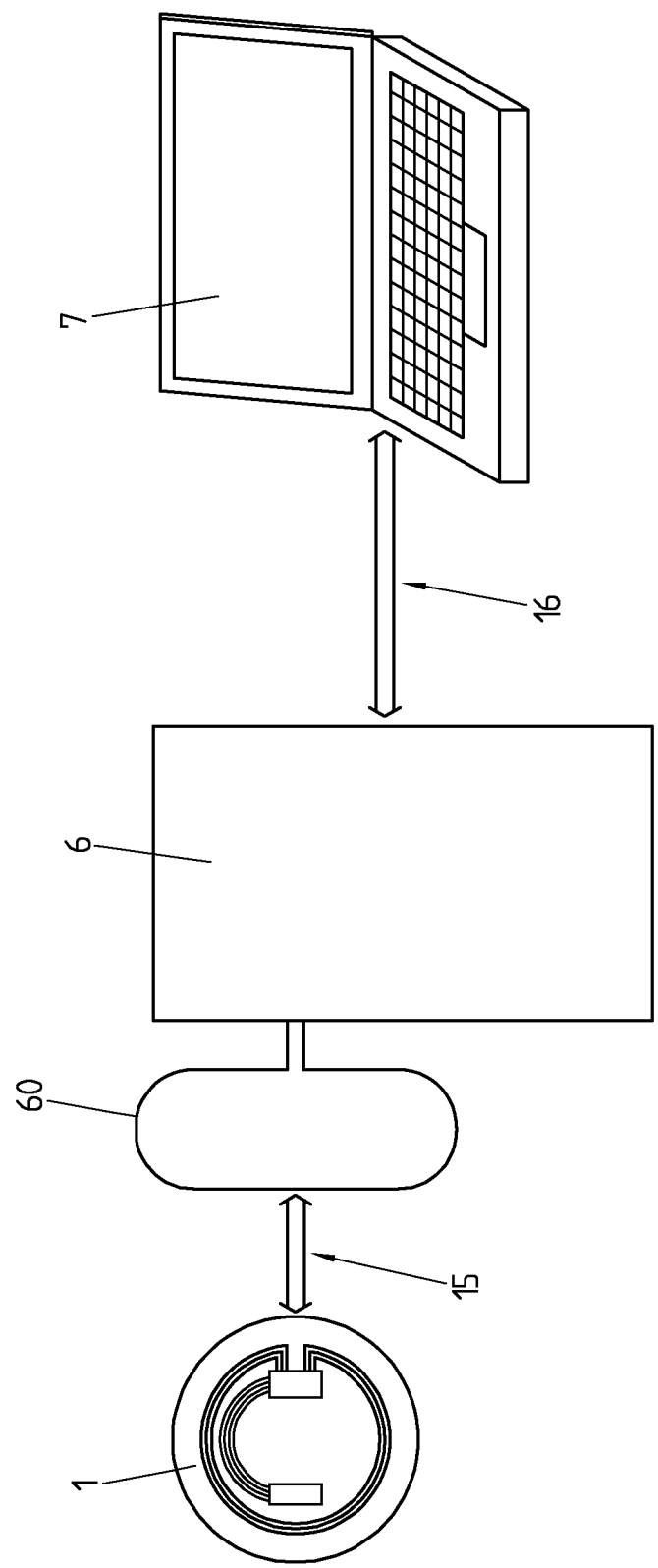
FIG. 7 is a schematic representation of an intraocular pressure monitoring system using an intraocular pressure monitoring device of the invention.

FIG. 7 is a schematic representation of a typical intraocular pressure monitoring system using the intraocular pressure measuring and/or monitoring device 1 of the invention. According to the illustrated embodiment, the intraocular pressure monitoring system comprises the intraocular pressure measuring and/or monitoring device 1 in the form of a soft contact lens with a pressure sensor, a portable recording device 6 for communicating with the pressure measuring and/or monitoring device 1 and storing the collected information during the IOP monitoring phases, and a computing device 7, for example a personal computer, for storing, analyzing, computing and/or displaying the data collected and stored by the portable communication device 6.

The portable recording device 6 comprises a first communication interface for communicating with the pressure measuring and/or monitoring device 1. The first communication interface is for example a wireless communication interface comprising an antenna 60 that is advantageously placed near the contact lens when the pressure measuring and/or monitoring device 1 of the invention is worn by a user. The antenna 60 is for example integrated into eyeglasses, not represented on the figures, and/or into a for example disposable, flexible and hypoallergenic patch, also not represented on the figures, that are or is worn by the user during the IOP monitoring periods. Other means are however possible within the frame of the invention for placing the antenna 60 at a suitable distance from the pressure measuring and/or monitoring device 1 when the latter is worn by a user. The portable recording device 6 further comprises a second communication interface for communicating with the computing device 7.

When monitoring IOP, the user wears the pressure measuring and/or monitoring device 1 by placing the contact lens on his or her eye, just like any ordinary contact lens, and carries the portable recording device 6, for example in a pocket or by hanging it around his or her neck. The antenna 60 is placed as close as possible to the user's eye wearing the pressure measuring and/or monitoring device 1 in order to allow the establishment of a first wireless communication channel 15 between the pressure measuring and/or monitoring device 1 and the recording device 6. Preferably, the antenna 60 is furthermore oriented in a plane as parallel as possible to the plane of the antenna of the pressure measuring and/or monitoring device 1 of the invention in order to allow for an efficient powering of the microprocessor and/or of the pressure sensor over the communication channel 15, which is for example a close distance inductive communication channel 15. The antenna is for example integrated in eyeglasses and/or into a patch surrounding the eye, for example into a disposable, flexible and hypoallergenic patch, and/or in a cap or in another piece of clothing or accessory worn by the user. Preferably, the antenna 60 is centered with the antenna of the pressure measuring and/or monitoring device 1 when the pressure measuring and/or monitoring device 1 and the portable recording device 6 are both worn by the user. The diameter of the antenna 60 of the portable recording device 6 is preferably larger than the diameter of the pressure measuring and/or monitoring device 1. The shape of the antenna 60 of the portable recording device 6 is for example round, oval, rectangular, or any other appropriate shape. The shape of the antenna 60 of the portable recording device 6 is preferably adapted to the shape of the device, for example the eyeglasses, the patch, the piece of garment, etc., to which it is attached.

According to an embodiment, while monitoring IOP, the portable recording device 6 powers the pressure measuring and/or monitoring device 1 through the first communication channel 15 at for example regularly spaced time intervals and collects data sent by the microprocessor through the antenna of the pressure measuring and/or monitoring device 1. Collected data for example comprises electrical resistance values of the gages of the pressure sensor and/or a IOP value calculated by a microprocessor of the pressure measuring and/or monitoring device 1. The collected data is stored in internal memory of the portable recording device 6. The intraocular pressure is for example measured at a frequency of 10 to 20 Hz during 10 to 60 seconds every 5 to 10 minutes. This allows a precise monitoring of the IOP variations over extended periods of time, including at night, while the user is asleep.

At some preferably predefined moments in time, for example once a day, once a week or once a month, the user and/or a practitioner connects the portable recording device 6 to a computing device 7, for example a personal computer, over a second, preferably wireless, communication channel 16, for example a Bluetooth communication channel. The second communication channel 16 can however also be a wired communication channel, for example a USB or any other appropriate communication channel. The data collected and stored in the internal memory of the portable recording device 6 is then transferred over the second communication channel 16 to the computing device 7 for further analysis and/or computing by the user and/or by the practitioner.

In variant embodiments, the intraocular pressure monitoring system comprises two pressure measuring and/or monitoring devices in order to allow simultaneously monitoring both eyes of a patient, for example over extended periods of time. Preferably, both pressure measuring and/or monitoring devices simultaneously and/or alternatively communicate with the same portable recording device 6 that for example is connected to and/or comprises two antennas. Accordingly, the portable recording device preferably stores or records data received from both intraocular pressure measuring and/or monitoring devices.

What is claimed is:

1. An intraocular pressure measuring and/or monitoring device comprising a soft contact lens and a pressure sensor united with said soft contact lens, said pressure sensor being located such that it is configured to be applied against an eye of a user for sensing the intraocular pressure (TOP) of said eye when said soft contact lens is worn by said user,
wherein said pressure sensor is located in a cavity formed in an inner concave side of said contact lens, and wherein said cavity is filled with a pressure transparent filler material that covers said pressure sensor such that a layer of said filler material is located between said pressure sensor and the surface of said eye when said user is wearing said contact lens, wherein said filler material is softer than the material of said soft contact lens.

2. The intraocular pressure measuring and/or monitoring device of claim 1, wherein said filler material is a silicone gel.

3. The intraocular pressure measuring and/or monitoring device of claim 1, wherein said cavity is a circular groove around the centre of said contact lens.

4. The intraocular pressure measuring and/or monitoring device of claim 1, wherein said cavity is formed in the centre of said contact lens.

5. The intraocular pressure measuring and/or monitoring device of claim 1, wherein an external surface of said filler material is convex.

6. The intraocular pressure measuring and/or monitoring device of claim 1, wherein an external surface of said filler material is structured.

7. A kit comprising:
an intraocular pressure measuring and/or monitoring device according to claim 1;
a portable recording device configured for communicating with said intraocular pressure measuring and/or monitoring device and for storing data received from said intraocular pressure measuring and/or monitoring device.

8. The kit of claim 7 wherein said portable recording device is configured for powering said intraocular pressure measuring and/or monitoring device over a wireless inductive communication channel.

9. The kit of claim 7, comprising two intraocular pressure measuring and/or monitoring devices, wherein said portable recording device is configured for communicating with said two intraocular pressure measuring and/or monitoring devices and for storing data received from said two intraocular pressure measuring and/or monitoring devices.

10. An intraocular pressure monitoring system comprising:
an intraocular pressure measuring and/or monitoring device according to claim 1;
a portable recording device configured for communicating with said pressure measuring and/or monitoring device and for storing data received from said intraocular pressure measuring and/or monitoring device;
a computing device configured for communicating with said portable recording device for receiving and/or processing and/or storing data received from said portable recording device.

11. The intraocular pressure monitoring system of claim 10, wherein said portable recording device is configured for powering said pressure measuring and/or monitoring device over a wireless inductive communication channel.

12. The intraocular pressure monitoring system of claim 10, comprising two intraocular pressure measuring and/or monitoring devices, wherein said portable recording device is configured for communicating with said two intraocular pressure measuring and/or monitoring devices and for storing data received from said two intraocular pressure measuring and/or monitoring devices.

13. An intraocular pressure measuring and/or monitoring device comprising a soft contact lens and a pressure sensor united with said soft contact lens, said pressure sensor being located such that it is configured to be applied against an eye of a user for sensing the intraocular pressure (TOP) of said eye when said soft contact lens is worn by said user,
wherein said pressure sensor is located in a cavity formed in an inner concave side of said contact lens, and wherein said cavity is filled with a pressure transparent filler material that covers said pressure sensor such that a layer of said filler material is located between said pressure sensor and the surface of said eye when said user is wearing said contact lens, wherein said filler material is a silicone gel.

14. The intraocular pressure measuring and/or monitoring device of claim 13, wherein said cavity is a circular groove around the centre of said contact lens.

15. The intraocular pressure measuring and/or monitoring device of claim 13, wherein said cavity is formed in the centre of said contact lens.

16. The intraocular pressure measuring and/or monitoring device of claim 13, wherein an external surface of said filler material is convex.

17. The intraocular pressure measuring and/or monitoring device of claim 13, wherein an external surface of said filler material is structured.

* * * * *